(12) United States Patent
Takenaga (10) Patent No.: US 8,391,323 B2
(45) Date of Patent: Mar. 5, 2013

(54) FIBER LASER DEVICE

(75) Inventor: Katsuhiro Takenaga, Sakura (JP)

(73) Assignee: Fujikura Ltd., Tokyo (JP)

( * ) Notice: Subject to any disclaimer, the term of this patent is extended or adjusted under 35 U.S.C. 154(b) by 4 days.

(21) Appl. No.: 13/168,660

(22) Filed: Jun. 24, 2011

(65) Prior Publication Data

US 2011/0286474 A1 Nov. 24, 2011

Related U.S. Application Data

(63) Continuation of application No. PCT/JP2009/007154, filed on Dec. 24, 2009.

(30) Foreign Application Priority Data

Dec. 26, 2008 (JP) ................................. 2008-333761

(51) Int. Cl.
*H01S 3/30* (2006.01)
(52) U.S. Cl. ............................................................ 372/6
(58) Field of Classification Search .................. 372/6, 3; 606/93; 362/553
See application file for complete search history.

(56) References Cited

U.S. PATENT DOCUMENTS

| 5,033,051 | A | * | 7/1991 | Werner | .............................. | 372/3 |
| 2009/0274175 | A1 | * | 11/2009 | Kitabayashi et al. | ............. | 372/3 |

FOREIGN PATENT DOCUMENTS

| JP | 46-37306 B2 | 11/1971 |
| JP | 03-032091 A | 2/1991 |
| JP | 2002-006348 A | 1/2002 |
| JP | 2007-221037 A | 8/2007 |
| WO | 2008/096863 A1 | 8/2008 |
| WO | 2009/001852 A1 | 12/2008 |

OTHER PUBLICATIONS

International Search Report for PCT/JP2009/007154, mailing date Feb. 9, 2010.

* cited by examiner

*Primary Examiner* — Jessica Stultz
*Assistant Examiner* — Tuan Nguyen
(74) *Attorney, Agent, or Firm* — Westerman, Hattori, Daniels & Adrian, LLP (57) ABSTRACT

A fiber laser device includes: a laser oscillator to emit laser light having a first wavelength; a first optical filter to transmit the laser light having the first wavelength; a wavelength converter to generate laser light having a second wavelength using stimulated Raman scattering caused by the laser light having the first wavelength and transmit the laser light having the first wavelength and the laser light having the second wavelength; and a second optical filter to transmit the laser light having the second wavelength and prevent transmission of laser light having the first wavelength. The laser light having the second wavelength that has passed through the second optical filter travels through an optical fiber amplifier and an output end. The first optical filter, the wavelength converter and the second optical filter are each constituted by a photonic band gap fiber.

5 Claims, 8 Drawing Sheets

FIBER LASER DEVICE

TECHNICAL FIELD

The invention relates to a fiber laser device.

BACKGROUND ART

In recent years, fiber laser devices are used in machines for machining utilizing laser light and in medical devices such as a surgical knife utilizing laser light. A fiber laser device is a device in which pulsed laser light emitted by a laser oscillator (master oscillator: MO) is amplified by an optical fiber amplifier (power amplifier: PA) and the amplified laser light is output through an output end.

Unfortunately, in a fiber laser device having such a configuration, part of laser light output toward an object to be irradiated may be reflected by the irradiated object and input to the fiber laser device through the output end thereof or laser light may be reflected at the output end. In such cases, the reflected laser light may be amplified again by the optical fiber amplifier and input to the laser oscillator, and may damage the laser oscillator.

In an attempt to prevent such damage caused by reflected laser light, Patent Document 1 discloses a fiber laser device including a wavelength converting fiber provided between a laser oscillator and an optical fiber amplifier, and further including a filter between the laser oscillator and the wavelength converting fiber. The wavelength converting fiber converts the wavelength of laser light having high intensity using stimulated Raman scattering. The filter transmits laser light having a wavelength emitted by the laser oscillator but blocks transmission of laser light having a wavelength obtained by converting the wavelength of the laser light emitted by the laser oscillator by the wavelength converting fiber.

In a fiber laser device having such a configuration, pulsed laser light output from the laser oscillator passes through the filter and is input to the wavelength converting fiber, but the wavelength thereof is not converted because the laser light has low intensity. Accordingly, the laser light having the wavelength as output from the laser oscillator is input from the wavelength converting fiber to the optical fiber amplifier, amplified thereby and output therefrom. Then, the laser light is directed to an object to be irradiated.

However, part of the laser light directed to the object to be irradiated may be reflected by the object and input to the fiber laser device through an output end thereof or the laser light may be reflected at the output end. In such a case, the reflected laser light is input to the optical fiber amplifier through the output end and amplified by the optical fiber amplifier. The amplified reflected laser light is input to the wavelength converting fiber. In this case, the wavelength of the reflected laser light is converted because the reflected laser light has high intensity as a result of being amplified. Then, the wavelength-converted reflected laser light is directed from the wavelength converting fiber to the laser oscillator, but is blocked by the filter before being input to the laser oscillator. According to the disclosure, it is thus possible to prevent the reflected laser light incident on the output end from being input to the laser oscillator and damaging the laser oscillator.

CITATION LIST

Patent Document

[Patent Document 1] Japanese Patent Application Laid-Open No. 2007-221037

SUMMARY OF INVENTION

Objects to be Achieved by the Invention

It is to be noted that the wavelength conversion is made using stimulated Raman scattering in the wavelength converting fiber in the fiber laser device disclosed in Patent Document 1. With the stimulated Raman scattering, the input laser light is converted to laser light having a longer wavelength. However, such wavelength conversion using stimulated Raman scattering may not convert the wavelength of the whole input light, but part of laser light having the wavelength as input may remain without being converted.

Therefore, when the wavelength of the reflected laser light, which is reflected by the object to be irradiated or at the output end and amplified by the optical fiber amplifier, is converted by the wavelength converting fiber, the laser light output from the wavelength converting fiber may contain the laser light having the wavelength that is not converted. Since the laser light having the wavelength that is not converted passes through the filter, part of the reflected laser light may be input to the laser oscillator and damage the laser oscillator.

Therefore, an object of the invention is to provide a fiber laser device capable of preventing laser light from damaging a laser oscillator even if the laser light is reflected by an object to be irradiated or at an output end.

Means for Achieving the Objects

A fiber laser device according to an aspect of the invention includes: a laser oscillator configured to emit laser light having a first wavelength; a first optical filter to which the laser light having the first wavelength output from the laser oscillator is input and which is configured to transmit the laser light having the first wavelength; a wavelength converter to which the laser light having the first wavelength that has passed through the first optical filter is input and which is configured to generate laser light having a second wavelength that is longer than the laser light having the first laser light using stimulated Raman scattering caused by the laser light having the first wavelength and transmit the laser light having the first wavelength and the laser light having the second wavelength; a second optical filter to which the laser light having the second wavelength output from the wavelength converter is input and which is configured to transmit the laser light having the second wavelength and prevent transmission of the laser light having the first wavelength; an optical fiber amplifier to which the laser light having the second wavelength that has passed through the second optical filter is input and which is configured to amplify the laser light having the second wavelength; and an output end through which the laser light having the second wavelength amplified by the optical amplifier is output, wherein the first optical filter prevents transmission of the laser light having the second wavelength, and the first optical filter, the wavelength converter and the second optical filter each include a photonic band gap fiber.

In such a fiber laser device, the laser light having the first wavelength output from the laser oscillator passes through the first filter and is input to the wavelength converter. Since the wavelength converter is configured to transmit laser light having the first wavelength, the laser light having the first wavelength input to the wavelength converter from the laser oscillator propagates through the wavelength converter. Then, in the wavelength converter, the laser light having the second wavelength that is longer than the first wavelength is generated by stimulated Raman scattering caused by the laser light having the first wavelength. The laser light having the second wavelength generated by the wavelength converter propagates through the wavelength converter and is output therefrom. The output laser light having the second wavelength is input to the second filter. At this time, since the second filter is configured to transmit laser light having the second wavelength but prevent transmission of laser light having the first wavelength, the second optical filter prevents the laser light having the first wavelength from being output and outputs the laser light having the second wavelength even if laser light having the first wavelength is contained in the laser light output from the wavelength converter. The laser light having the second wavelength that has passed through the second optical filter is amplified by the optical fiber amplifier and output through the output end.

Part of the laser light output through the output end may be reflected by an object to be irradiated and input to the optical fiber amplifier through the output end or may be reflected at the output end. In such cases, the reflected laser light is input to the optical fiber amplifier and amplified thereby. The reflected laser light is then input to the second optical filter. Since the second optical filter is configured to transmit laser light having the second wavelength, the reflected laser light passes through the second filter. The reflected laser light that has passed through the second filter is input to the wavelength converter. Since the wavelength converter transmits laser light having the second wavelength, the reflected laser light is output from the wavelength converter. The reflected laser light output from the wavelength converter is input to the first optical filter. Since the first optical filter is configured to prevent transmission of laser light having the second wavelength, the reflected laser light is not input to the laser oscillator, which can prevent the laser oscillator from being damaged or the like.

Moreover, since the first optical filter, the wavelength converter and the second optical filter each include a photonic band gap fiber (PBGF), losses of the laser light having the first wavelength that has passed through the first optical filter and the laser light having the second wavelength that has passed through the wavelength converter and the second optical filter are very little in the first optical filter, the wavelength converter and the second optical filter. In addition, since the first optical filter and the second optical filter are constituted by the PBGF as described above, the first optical filter is excellent in preventing transmission of the laser light having the second wavelength, and the second optical filter is excellent in preventing transmission of the laser light having the first wavelength. Therefore, the fiber laser device can output laser light with high intensity and also effectively prevent the reflected laser light from damaging the laser oscillator or the like.

Furthermore, in the fiber laser device described above, the wavelength converter is preferably configured to prevent transmission of laser light having a third wavelength longer than the second wavelength generated by stimulated Raman scattering caused by the laser light having the second wavelength. With such a configuration of the wavelength converter, since the laser light having the third wavelength that is second-order Raman scattering light is prevented from being generated, energy of the laser light having the second wavelength is prevented from being used for generating laser light having the third wavelength. As a result, it is possible to increase the intensity of laser light having the second wavelength output from the wavelength converter.

In the fiber laser device described above, the first optical filter is preferably configured to prevent transmission of the laser light having the third wavelength. If laser light having the second wavelength λ2 is input to the wavelength converter as reflected laser light, laser light having the third wavelength may be generated by Raman scattering caused by the reflected laser light having the second wavelength λ2 in the wavelength converter. In this case, even if the laser light having the third wavelength is input to the first optical filter, the laser light having the third wavelength is prevented from passing through the first optical filter according to such a configuration. Thus, the laser light having the third wavelength is prevented from being input to the laser oscillator or the like, and it is possible to effectively prevent the reflected laser light having the third wavelength from damaging the laser oscillator or the like.

In the fiber laser device described above, the first optical filter may have a cross sectional shape homologous to that of the second optical fiber.

More preferably, in the fiber laser device described above, the first optical filter, the wavelength converter and the second optical filter are continuously produced from one optical fiber preform. With such a configuration, the first optical filter, the wavelength converter and the second optical filter may be formed of one PBGF without any fused portions between the first optical filter, the wavelength converter and the second optical filter. Therefore, the fiber laser device can have a simple configuration and the production cost thereof can be kept low. Furthermore, losses of laser light at boundaries between the first optical filter, the wavelength converter and the second optical filter can be reduced and the fiber laser device can output laser light with higher intensity.

Effect of the Invention

According to the invention, a fiber laser device capable of preventing laser light from damaging a laser oscillator even if the laser light is reflected by an object to be irradiated or at an output end.

BEST MODE FOR CARRYING OUT THE INVENTION

A suitable embodiment of a fiber laser device according to the invention will be described in detail below referring to the drawings.

Figure 1:
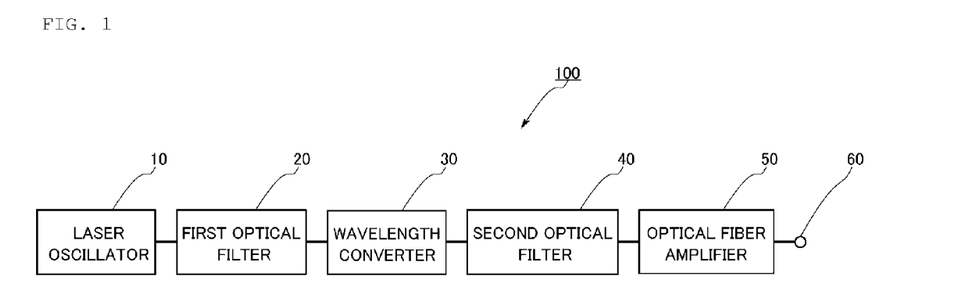
FIG. 1 is a diagram showing a fiber laser device according to the invention.

FIG. 1 is a diagram showing a fiber laser device according to the invention.

As shown in FIG. 1, a fiber laser device 100 includes: a laser oscillator 10 configured to output laser light having a first wavelength λ1; a first optical filter 20 connected to the laser oscillator 10 so that the laser light from the laser oscillator 10 is input to the first optical filter 20; a wavelength converter 30 connected to the first optical filter 20 so that the laser light having the first wavelength λ1 from the first optical filter 20 is input to the wavelength converter 30, and configured to generate laser light having a second wavelength λ2; a second optical filter 40 connected to the wavelength converter 30 so that the laser light from the wavelength converter 30 is input to the second optical filter 40; an optical fiber amplifier 50 connected to the second optical filter 40 so that the laser light from the second optical filter 40 is input to the optical fiber amplifier 50; and an output end 60 through which laser light amplified by the optical fiber amplifier 50 is output.

(Laser Oscillator)

Figure 2:
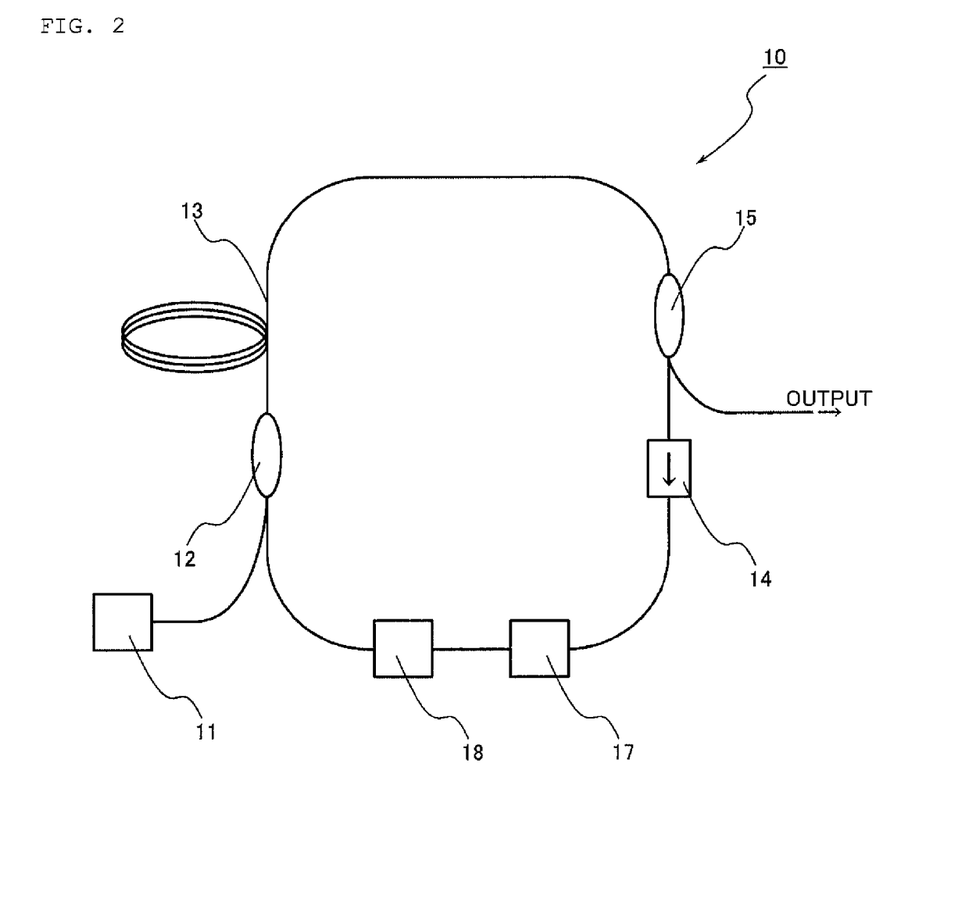
FIG. 2 is a diagram showing a laser oscillator shown in FIG. 1.

FIG. 2 is a diagram showing an example of the laser oscillator 10. In this embodiment, a fiber ring laser is used as the laser oscillator 10. As shown in FIG. 2, the laser oscillator 10 includes: a pumping light source 11; a WDM coupler 12 connected to the pumping light source 11; a rare earth-doped fiber 13 connected to the WDM coupler 12; an output coupler 15 connected to the rare earth-doped fiber 13; an optical isolator 14 connected to the output coupler 15; a band-pass filter 17 connected to the optical isolator 14; and an optical switch 18 connected to the WDM coupler 12 that is connected to the band-pass filter 17.

Pumping light output from the pumping light source 11 is input to the rare earth-doped fiber 13 through the WDM coupler 12. In the rare earth-doped fiber 13, the pumping light is absorbed by rare-earth ions doped in the rare earth-doped fiber 13. As a result, the rare earth ions are pumped. Then, the pumped rare earth ions emit light of a predetermined wavelength. The light is amplified while propagating through the rare earth-doped fiber 13. The amplified light is input to the band-pass filter 17 through the output coupler 15 and the optical isolator 14, and the wavelength band thereof is limited by the band-pass filter 17. The optical isolator 14 blocks excess reflected light or the like. The band-limited light is input again to the rare earth-doped fiber 13 through the optical switch 18 and the WDM coupler 12, and amplified therein. In this case, the optical switch 18 periodically repeats a low loss state and a high loss state. Accordingly, light having low intensity and light having high intensity are input periodically to the rare earth-doped fiber 13. As a result, in the laser oscillator 10, pulsed light is amplified, and the amplified pulsed light is output as laser light through the output coupler 15.

The laser oscillator 10 outputs laser light having the first wavelength λ1. The first wavelength λ1 is 1040 nm, for example.

(First Optical Filter)

Figure 3:
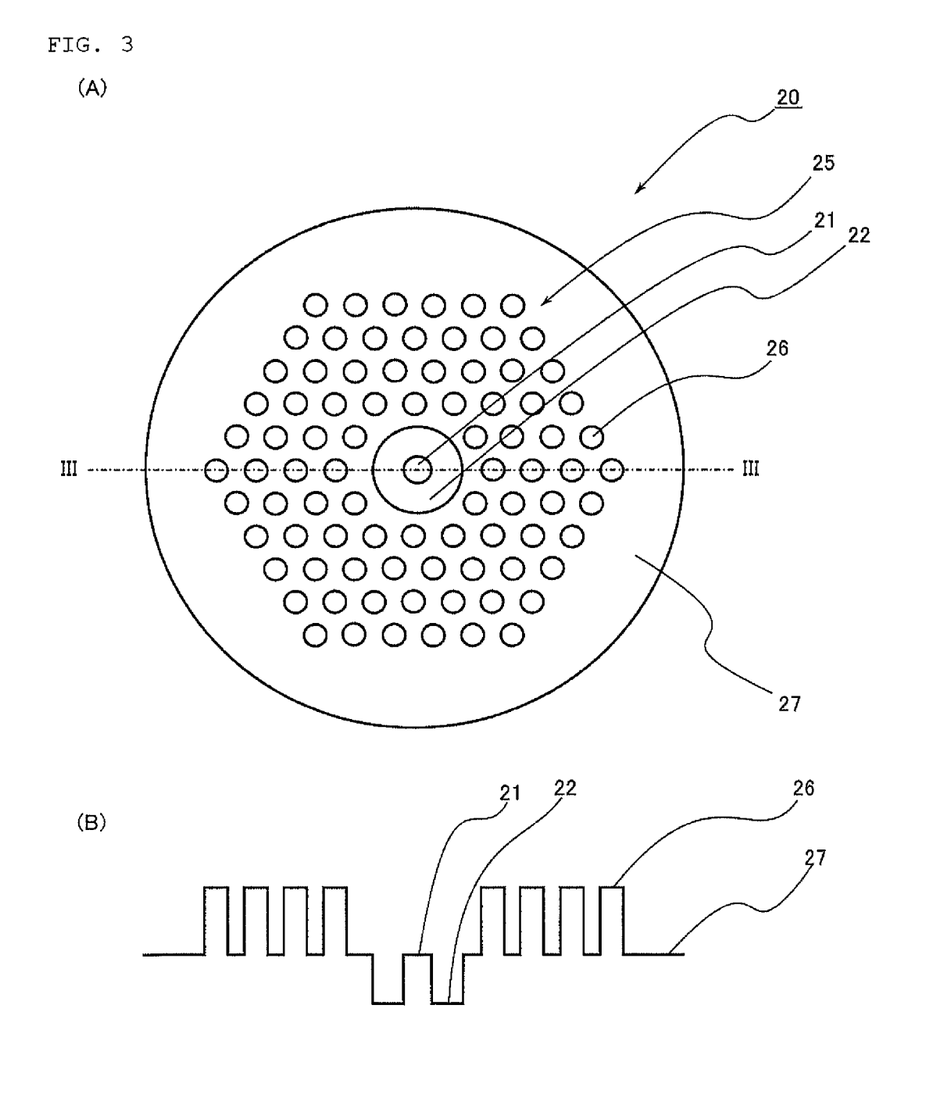
FIG. 3 shows a sectional view of a first optical filter and a graph showing a refractive index distribution of the first optical filter.

FIG. 3 shows a sectional view showing a cross sectional structure perpendicular to a long axis direction of an optical fiber constituting the first optical filter 20 and a graph showing a refractive index distribution of the optical fiber constituting the first optical filter 20. Specifically, FIG. 3(B) is a graph showing the refractive index at line III-III in FIG. 3(A).

As shown in FIG. 3(A), the first optical filter 20 is constituted by a PBGF including a first core 21, a second core 22 coating the first core 21, a periodic structure region 25 having a number of high refractive index portions 26 of a cylindrical shape arranged in a region surrounding the second core 22, and a clad region 27 surrounding the periodic structure region 25. Specifically, some of the high refractive index portions 26 are arranged in a manner surrounding the second core 22 in a hexagonal shape. The other high refractive index portions 26 are arranged in a triangular grid based on the high refractive index portions 26 arranged in a hexagonal shape, and a space between adjacent high refractive index portions 26 is filled with the same material as that for the clad region 27. A region in which the high refractive index portions 26 are arranged constitutes the periodic structure region 25. Although the periodic structure of the high refractive index portions 26 in the periodic structure region 25 includes four layers in this embodiment as shown in FIG. 3(A), the periodic structure is not limited to four layers.

As shown in FIG. 3(B), the second core 22 has a lower refractive index than the first core 21. The high refractive index portions 26 have a higher refractive index than the first core 21. In order to obtain such refractive indices, the first core 21 is made of silica without any dopant, for example. The second core 22 is made of silica doped with a dopant, such as fluorine or boron, that lowers the refractive index, for example. The high refractive index portions 26 are made of silica doped with a dopant, such as germanium, that increases the refractive index. In addition, the clad region 27 is made of silica without any dopant. Note that germanium or phosphorus may be doped in the first core 21. Even in this case, the first core 21 is made so that the refractive index thereof is lower than that of the high refractive index portions 26. In addition, if germanium or phosphorus is not doped as a dopant in the first core 21 or if the doping amount thereof is small, the nonlinear constant is small. Therefore, it is preferable that the doping amount is small in the first core 21 or the first core 21 is not doped with any dopant in terms of preventing the wavelength of the laser light from becoming wider as a result of the nonlinear optical effect and obtaining an output with a narrow wavelength spectrum.

Figure 4:
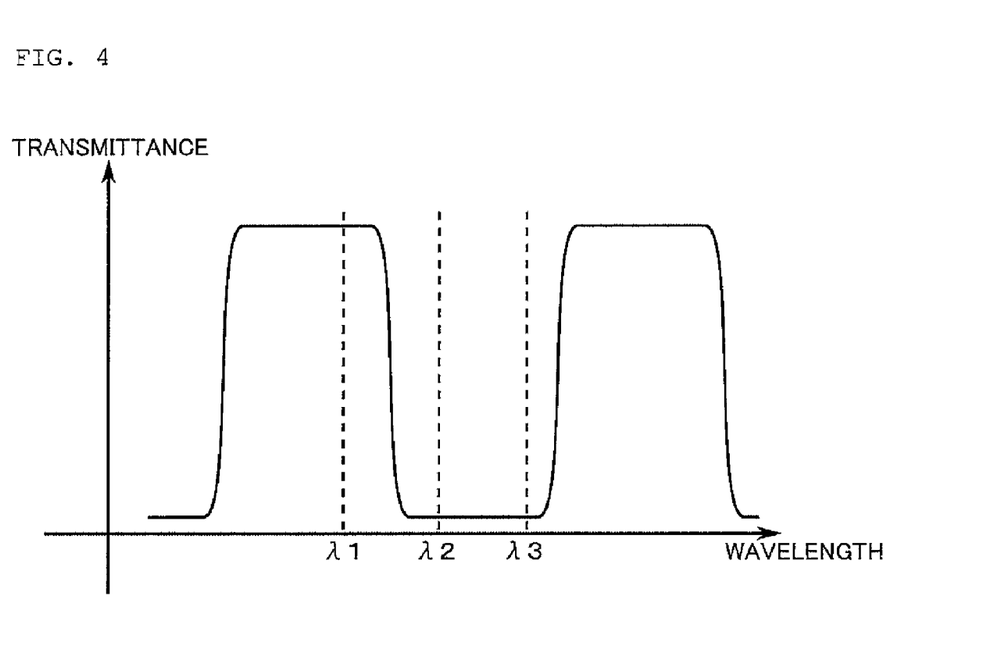
FIG. 4 is a graph showing light transmission characteristics of the first optical filter with respect to wavelength.

FIG. 4 is a graph showing light transmission characteristics of the first optical filter 20 shown in FIG. 3 with respect to the wavelength. As described above, the PBGF is used for the first optical filter 20. As shown in FIG. 4, the light transmission characteristics of the first optical filter 20 with respect to the wavelength are those in which a wavelength range in which light passes through the first optical filter 20 and a wavelength range in which transmission of light is prevented are repeated at every certain wavelength because of the properties of the PBGF.

The first optical filter 20 is configured to transmit laser light having the first wavelength λ1 output from the laser oscillator 10, but prevent transmission of laser light having the second wavelength λ2 converted from the light having the first wavelength λ1 by the wavelength converter 30. In addition, the first optical filter 20 is configured to prevent transmission of light having a third wavelength λ3 that is second-order Raman light of the light having the first wavelength λ1 in this embodiment. Note that the wavelength range in which light passes through the first optical filter 20 and the wavelength range in which transmission of light is prevented in the first optical filter 20 can be set by adjusting the size or the relative refractive index difference of the core region or the intervals or the relative refractive index difference of the high refractive index portions 26 of the PBGF constituting the first optical filter 20. For example, a specific configuration of the first optical filter 20 shown in FIG. 3 may be as follows: the PBGF has a diameter of 190 μm, the first core 21 has a diameter of 4.2 μm, the relative refractive index difference of the first core 21 with respect to silica is 0.0%, the center to center distance of the high refractive index portions 26 is 8.2 μm, the relative refractive index difference of the high refractive index portions 26 with respect to silica is 2.75%, the high refractive index portions 26 have a diameter of 5.1 µm, and the relative refractive index difference of the second core 22 with respect to silica is −0.7%. In this case, the first optical filter 20 transmits light having a wavelength λ1 of 1040 nm, prevents transmission of light having a wavelength λ2 of 1090 nm, and prevents transmission of light having a wavelength λ3 of 1140 nm.

(Wavelength Converter)

Figure 5:
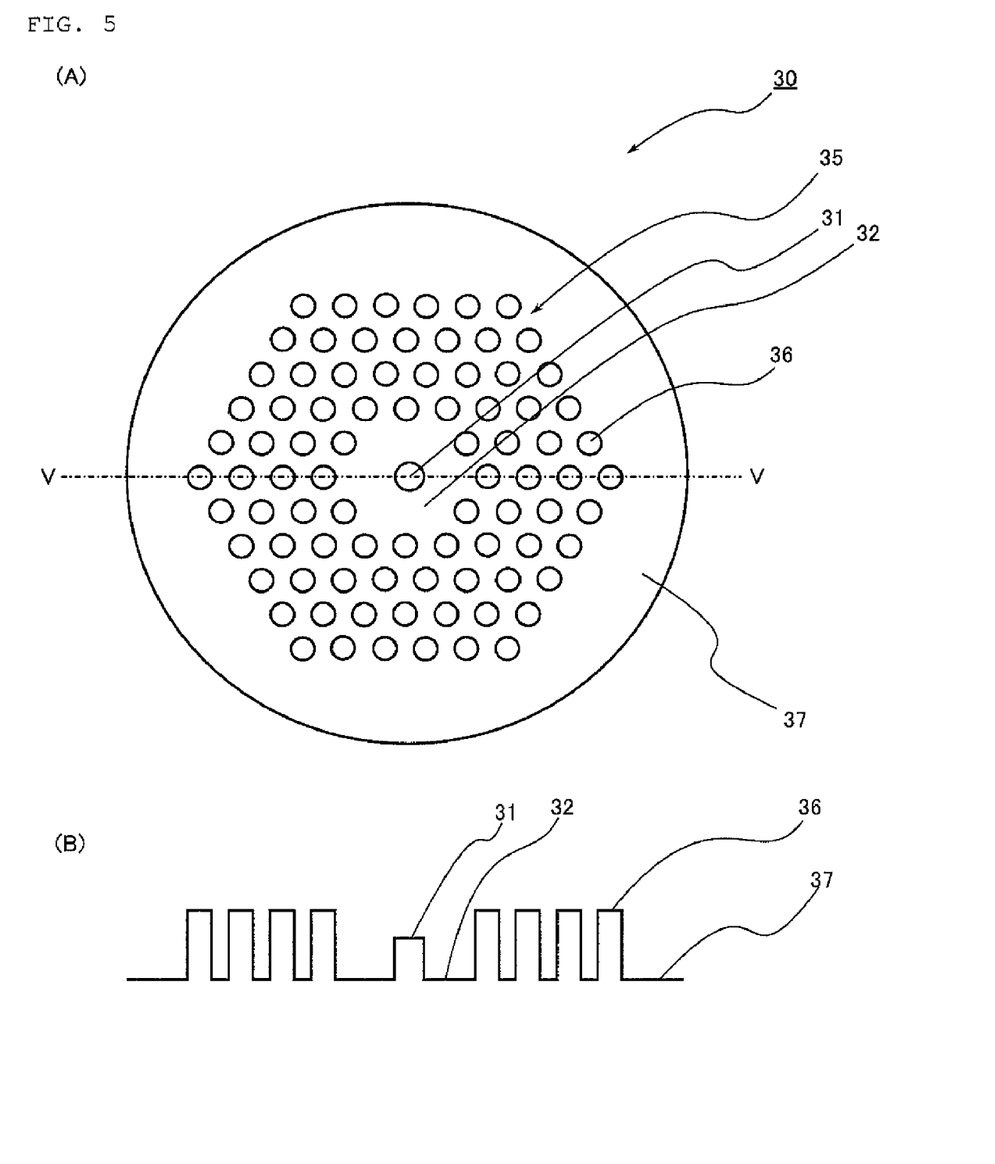
FIG. 5 shows a sectional view of a wavelength converter and a graph showing a refractive index distribution of the wavelength converter.

FIG. 5 shows a sectional view showing a cross sectional structure perpendicular to a long axis direction of an optical fiber constituting the wavelength converter 30 and a graph showing a refractive index distribution of the optical fiber constituting the wavelength converter 30. Specifically, FIG. 5(B) is a graph showing the refractive index at line V-V in FIG. 5(A).

As shown in FIG. 5(A), the wavelength converter 30 is constituted by a PBGF including a core 31, a core region 32 coating the core 31, a periodic structure region 35 having a number of high refractive index portions 36 of a cylindrical shape arranged in a region surrounding the core region 32, and a clad region 37 surrounding the periodic structure region 35. Specifically, some of the high refractive index portions 36 are arranged in a manner surrounding the core region 32 in a hexagonal shape. The other high refractive index portions 36 are arranged in a triangular grid based on the high refractive index portions 36 arranged in a hexagonal shape, and a space between adjacent high refractive index portions 36 is filled with the same material as that for the clad region 37. A region in which the high refractive index portions 36 are arranged constitutes the periodic structure region 35. Although the periodic structure of the high refractive index portions 36 in the periodic structure region 35 includes four layers in this embodiment as shown in FIG. 5(A), the periodic structure is not limited to four layers.

As shown in FIG. 5(e), the core region 32 has a refractive index equal to that of the clad region 37. The core 31 has a higher refractive index than the core region 32. In addition, the high refractive index portions 36 have a higher refractive index than the core 31. In order to obtain such refractive indices, the core region 32 and the clad region 37 are made of silica without any dopant, for example. The core 31 and the high refractive index portions 36 are made of silica doped with a dopant, such as germanium, that increases the refractive index. However, the doping amounts of the dopants and the like are adjusted so that the refractive indices of the core 31 and the high refractive index portions 36 satisfy the relationship as described above. The dopant of the core 31 is preferably germanium or phosphorus that increases the non-linear constant in terms of efficiently generating stimulated Raman scattering.

Figure 6:
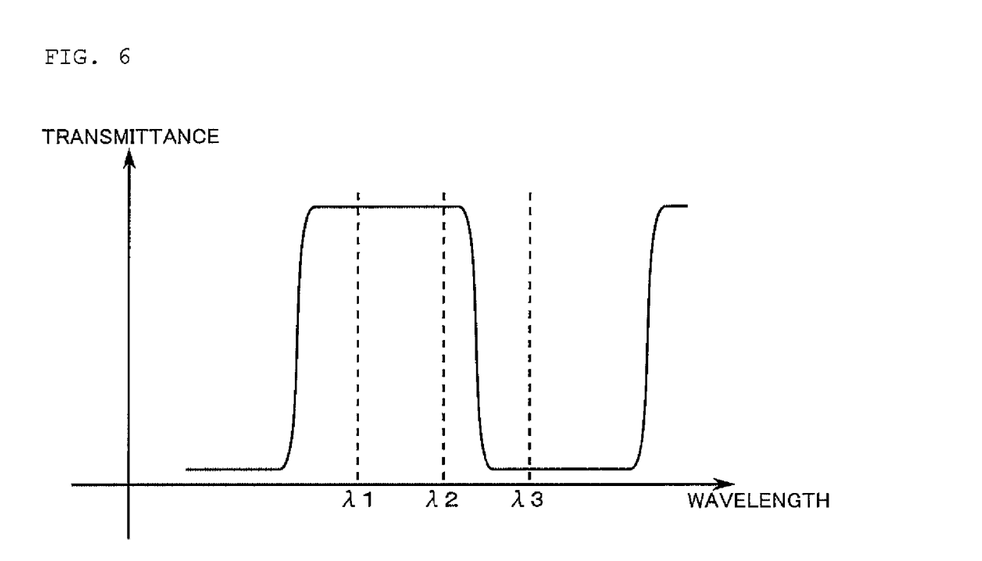
FIG. 6 is a graph showing light transmission characteristics of the wavelength converter with respect to wavelength.

FIG. 6 is a graph showing light transmission characteristics of the wavelength converter 30 with respect to the wavelength. Since the wavelength converter 30 is constituted by the PBGF as described above, the light transmission characteristics of the wavelength converter 30 with respect to the wavelength are those in which a wavelength range in which light passes through the wavelength converter 30 and a wavelength range in which transmission of light is prevented are repeated at every certain wavelength. The wavelength converter 30 is configured to transmit laser light having the first wavelength λ1 output from the laser oscillator 10 and laser light having the second wavelength λ2. In addition, the wavelength converter 30 is configured to prevent transmission of laser light (second-order Raman scattering light) having the third wavelength λ3 longer than the second wavelength λ2 generated by stimulated Raman scattering caused by the laser light having the second wavelength λ2.

Note that the wavelength range in which light passes through the wavelength converter 30 and the wavelength range in which transmission of light is prevented in the wavelength converter 30 can be set by adjusting the size or the relative refractive index difference of the core region or the intervals or the relative refractive index difference of the high refractive index portions 36 of the PBGF constituting the wavelength converter 30. For example, a specific configuration of the wavelength converter 30 shown in FIG. 5 may be as follows: the PBGF has a diameter of 136 µm, the core 31 has a diameter of 4.4 µm, the relative refractive index difference of the core 31 with respect to silica is 0.7%, the center to center distance of the high refractive index portions 36 is 5.9 µm, the relative refractive index difference of the high refractive index portions 36 with respect to silica is 2.7%, and the high refractive index portions 36 have a diameter of 3.7 µm. In this case, the wavelength converter 30 transmits light having the wavelength λ1 of 1040 nm, transmits light having the wavelength λ2 of 1090 nm, and prevents transmission of light having the wavelength λ3 of 1140 nm.

When laser light having the first wavelength λ1 is input to the wavelength converter 30, laser light having the second wavelength λ2 that is longer than the first wavelength λ1 is generated by stimulated Raman scattering caused by the laser light having the first wavelength λ1. The wavelength converter 30 thus outputs the laser light having the second wavelength λ2. For example, if laser light having a wavelength of 1040 nm as the first wavelength λ1 is input, laser light having a wavelength of 1090 nm as the second wavelength λ2 is generated. However, if part of the laser light having the first wavelength λ1 is not converted into laser light having the second wavelength λ2 by stimulated Raman scattering, the wavelength converter 30 outputs laser light having the first wavelength λ1 together with laser light having the second wavelength λ2.

In this embodiment as described above, the wavelength converter 30 is also configured to prevent transmission of laser light having the third wavelength λ3 that is stimulated Raman scattering light caused by laser light having the second wavelength λ2. For example, if stimulated Raman scattering light having a wavelength of 1090 nm is generated as laser light having the second wavelength λ2, a little amount of laser light having a wavelength of 1140 nm is generated as the second-order Raman scattering light, which is prevented from passing. Since transmission of laser light having the third wavelength that is second-order Raman scattering light is prevented in this manner, laser light having the third wavelength that is second-order Raman scattering light is prevented from being generated in the wavelength converter 30. As a result, it is possible to prevent energy of the laser light having the second wavelength from being used for generating laser light having the third wavelength, which allows the laser light having the second wavelength λ2 output from the wavelength converter 30 to have higher intensity.

Figure 7:
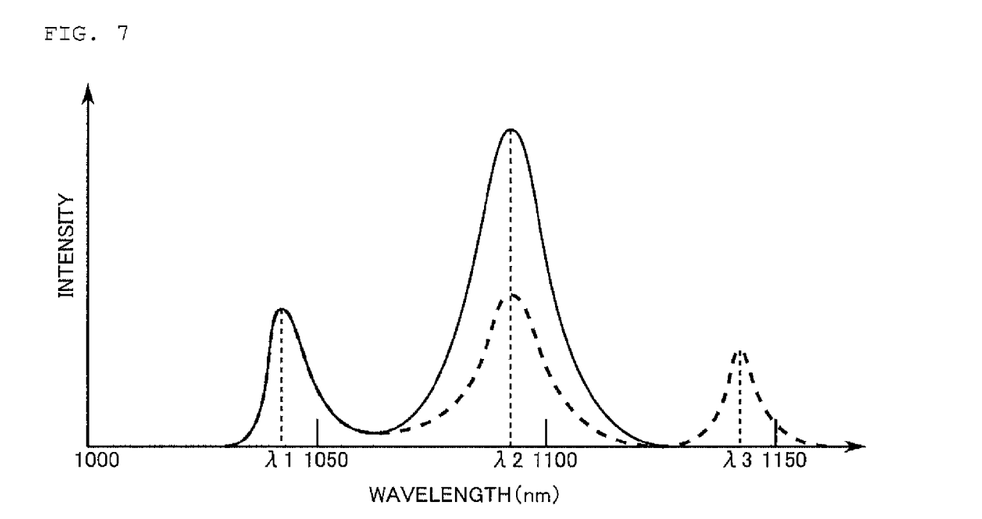
FIG. 7 is a graph showing an example of intensity of laser light output from the wavelength converter.

FIG. 7 is a graph showing an example of a spectrum of laser light output from such a wavelength converter 30 including the PBGF in which laser light having the third wavelength λ3 is prevented from being generated. In FIG. 7 a spectrum of light output when laser light having a wavelength of 1040 nm as the first wavelength λ1 is input and laser light having a wavelength of 1090 nm as the second wavelength λ2 is generated. As shown in FIG. 7, laser light having the third wavelength is prevented from being generated and the intensity of laser light having the second wavelength λ2 is high in the light output from the wavelength converter 30. A broken line shows a spectrum of light output from the wavelength converter in a case where a wavelength converting optical fiber that does not prevent generation of laser light having the third wavelength $\lambda 3$ is used as the wavelength converter instead of the PBGF. The conditions under which the spectrum is obtained are the same as those for the spectrum in the case where the PBGF is used except that generation of laser light having the third wavelength $\lambda 3$ is not prevented. As shown by the broken line, since part of laser light having the second wavelength $\lambda 2$ is converted into laser light having the third wavelength $\lambda 3$ in the case where the wavelength converting optical fiber that is not PBGF is used as the wavelength converter, the spectrum intensity of the laser light having the second wavelength $\lambda 2$ as compared to that of the laser light having the first wavelength $\lambda 1$ is smaller than in the case where the PBGF that prevents generation of laser light having the third wavelength $\lambda 3$ is used.

(Second Filter)

The second optical filter 40 is constituted by a PBGF. The PBGF constituting the second optical filter 40 is made of the same material as the PBGF constituting the first optical filter 20 and has a cross sectional structure homologous to that of the PBGF of the first optical filter 20.

Figure 8:
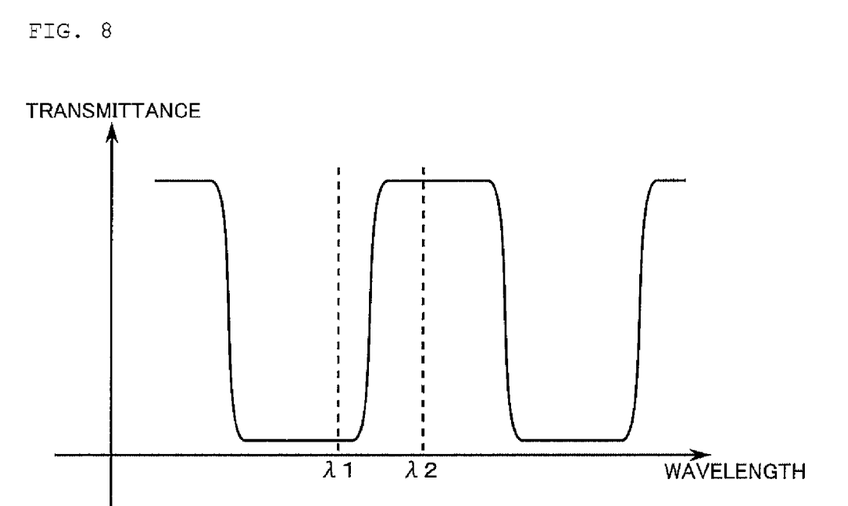
FIG. 8 is a graph showing light transmission characteristics of a second optical filter with respect to wavelength.

FIG. 8 is a graph showing light transmission characteristics of the second optical fiber 40 with respect to the wavelength. Since the PBGF is used for the second optical filter 40 as described above, the second optical filter 40 has transmission characteristics in which a wavelength range in which light passes therethrough and a wavelength range in which transmission of light is prevented are alternatively repeated at every certain wavelength. The second optical filter 40 is configured to transmit light having the second wavelength $\lambda 2$ and prevent transmission of light having the first wavelength $\lambda 1$ in the relationship between the wavelength ranges and the second wavelength $\lambda 2$ and the first wavelength $\lambda 1$. Accordingly, even when laser light having the first wavelength $\lambda 1$ is output from the wavelength converter 30 together with laser light having the second wavelength $\lambda 2$, the second optical filter 40 does not output light having the first wavelength $\lambda 1$ and outputs only light having the second wavelength $\lambda 2$.

Note that the wavelength range in which light passes through the second optical filter 40 and the wavelength range in which transmission of light is prevented in the second optical filter 40 can be set by adjusting the size or the relative refractive index difference of the core region or the intervals or the relative refractive index difference of the high refractive index portions of the PBGF constituting the second optical filter 40. Therefore, the wavelength range in which light passes and the wavelength range in which transmission of light is prevented can be set by changing the diameter of the PBGF of the second optical filter 40 so that the cross sectional shape of the PBGF is homologous to that of the first optical filter 20. For example, a specific configuration of the optical filter 40 may be as follows: the PBGF has a diameter of 160 μm, the core has a diameter of 3.5 μm, the relative refractive index difference of the core with respect to silica is 0.0%, the center to center distance of the high refractive index portions is 6.9 μm, the relative refractive index difference of the high refractive index portions with respect to silica is 2.75%, the high refractive index portions have a diameter of 4.3 μm, and the relative refractive index difference of the second core with respect to silica is −0.7%. In this case, the second optical filter 40 prevents transmission of light having the wavelength $\lambda 1$ of 1040 nm and transmits light having the wavelength $\lambda 2$ of 1090 nm.

(Optical Fiber Amplifier)

Figure 9:
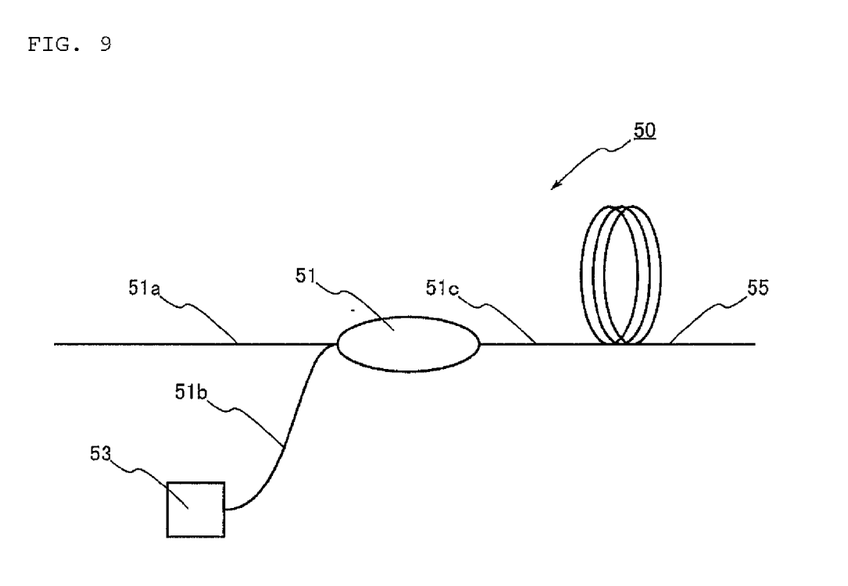
FIG. 9 is a diagram showing a configuration of an optical fiber amplifier.

FIG. 9 is a diagram showing a configuration of the optical fiber amplifier 50. The optical fiber amplifier 50 includes: a pumping light source 53; an optical coupler 51 to which pumping light from the pumping light source 53 and laser light having the second wavelength from the second optical filter 40 are input and which is configured to output pumping light and laser light having the second wavelength; and an amplification optical fiber 55 to which the pumping light and the laser light having the second wavelength output from the optical coupler 51 are input and which is configured to amplify the laser light having the second wavelength.

The pumping light source 53 outputs pumping light for pumping rare earth elements doped in the amplification optical fiber 55.

The optical coupler 51 has an input port 51a through which the laser light from the second optical filter 40 is input, a pumping light input port 51b through which the pumping light from the pumping light source 53 is input and an output port 51c through which the laser light and the pumping light from the second optical filter 40 are output. The input port 51a is constituted by a single mode fiber that allows the laser light having the second wavelength $\lambda 2$ to propagate in single mode. The pumping light input port 51b is constituted by a multi mode fiber that allows the pumping light output from the pumping light source 53 to propagate in multi mode. The output port 51c has a core portion and a clad portion, and is configured to allow laser light having the second wavelength $\lambda 2$ to propagate through the core portion in single mode and allow pumping light to propagate through the core portion and the clad portion in multi mode.

The amplification optical fiber 55 has a core portion doped with rare earth elements and a clad portion coating the core portion. The core portion allows the laser light having the second wavelength $\lambda 2$ output from the optical fiber coupler to propagate as single mode light, and the core portion and the clad portion allow the pumping light to propagate as multi mode light. Then, the pumping light pumps the rare earth elements doped in the core portion while passing through the core portion, and the laser light having the second wavelength $\lambda 2$ propagating therethrough is amplified by a stimulated emission phenomenon. Note that the amplification optical fiber 55 may allow the laser light having the second wavelength $\lambda 2$ to propagate as multi mode light.

(Output End)

The output end 60 outputs the laser light amplified in the optical fiber amplifier 50 to outside of the fiber laser device 100. Since the laser oscillator 10 is configured to output pulsed laser light as described above, pulsed laser light is output from the output end 60.

Next, operations of the fiber laser device 100 having the configuration as described above will be described.

As shown in FIG. 1, the laser light having the wavelength $\lambda 1$ output from the laser oscillator 10 is input to the first optical filter 20. Since the first optical filter 20 is configured to transmit laser light having the first wavelength $\lambda 1$, the laser light passes through the first optical filter 20. The laser light that has passed through the first optical filter 20 is wavelength-converted into laser light having the second wavelength $\lambda 2$ by the wavelength converter 30. The laser light having the second wavelength $\lambda 2$ as a result of the wavelength conversion is input to the second optical filter 40. In this case, if laser light having the first wavelength $\lambda 1$ remains in the laser light output from the wavelength converter 30, the laser light having the first wavelength $\lambda 1$ is also input to the second optical filter 40. However, since the second optical filter 40 is configured to transmit laser light having the second wavelength λ2 and prevent transmission of laser light having the first wavelength λ1, the second optical filter 40 only outputs the laser light having the second wavelength λ2. The laser light having the wavelength λ2 output from the second optical filter 40 is input to and amplified by the optical fiber amplifier 50, and output through the output end 60. The laser light having the second wavelength λ2 is output from the fiber laser device 100 in this manner.

The laser light output from the fiber laser device 100 is directed to the object to be irradiated. At this time, part of the laser light directed to the object to be irradiated may be reflected by the object and incident on the output end 60 as reflected laser light or may be reflected at the output end. Such reflected laser light has the second wavelength λ2. The reflected laser light is input to the optical fiber amplifier 50. Since the optical fiber amplifier 50 is configured to amplify laser light having the second wavelength λ2, the reflected laser light is amplified thereby. The amplified reflected laser light is input to the second optical filter 40 from the optical fiber amplifier 50. Since the second optical filter 40 is configured to transmit laser light having the second wavelength λ2, the reflected laser light passes through the second optical filter 40. The reflected laser light that has passed through the second optical filter 40 is input to the wavelength converter 30. Since the wavelength converter 30 is configured to transmit laser light having the second wavelength λ2, the reflected laser light passes through the wavelength converter 30. The reflected laser light that has passed through the wavelength converter 30 is input to the first optical filter 20. However, the first optical filter 20 is configured to prevent transmission of laser light having the second wavelength λ2. Therefore, the reflected laser light is prevented from being input to the laser oscillator 10 from the first optical filter 20, which prevents the laser oscillator 10 from being damaged.

In the fiber laser device 100 described above, even if the reflected laser light having the second wavelength λ2 is input to the wavelength converter 30, where laser light having the third wavelength is generated by stimulated Raman scattering of the reflected laser light having the second wavelength λ2, and the laser light having the third wavelength is input to the first optical filter 20, the laser light having the third wavelength is prevented from passing through the first optical filter 20. Accordingly, the laser light having the third wavelength is prevented from being input to the laser oscillator 10, and it is thus possible to effectively prevent the laser oscillator 10 from being damaged or the like by the reflected laser light having the third wavelength.

Next, a method for producing the PBGF constituting the first optical filter 20 will be described.

First, a silica glass rod made of silica glass, which will be the first core 21; a silica tube doped with a dopant such as fluorine and boron, which will be the second core 22; two-layer silica glass rods each having a center portion made of silica glass doped with a dopant such as germanium and having a higher refractive index than silica glass and an outer layer portion made of silica glass provided around the center portion, which will be the high refractive index portions 26; and a silica tube made of silica glass in which a through-hole having a circular cross section is formed, which will be the clad region 27, are prepared. The number of the two-layer silica glass rods to be prepared is the same as that of the high refractive index portions 26.

Next, the silica glass rod to be the first core 21 is inserted into the silica tube to be the second core 22. Then, the silica tube to be the second core 22 in which the silica glass rod to be the first core 21 is inserted is positioned at the center of the through-hole formed in the silica tube to be the clad region 27. Then, the two-layer silica glass rods are positioned around the silica tube to be the second core 22 in a closely packed manner. In this case, the size of the through-hole is adjusted in advance so that all the two-layer silica glass rods fit into the through-hole of the silica tube to be the clad region 27. If the first core 21 is to be doped with a dopant such as germanium, the dopant such as germanium is added to the silica glass rod to be the first core 21.

Next, a lower end of the silica tube in which the silica glass rod to be the first core 21, the silica tube to be the second core 22 and the two-layer silica glass rods are arranged is sealed, and a cap is attached to an upper end thereof so that the silica tube is hermetically closed. In this manner, an optical fiber preform is obtained. Then, the optical fiber preform is heated in a heating furnace of a drawing apparatus to draw a fiber while evacuating the silica tube through the cap. Then, the drawn glass is cooled and solidified. In this manner, the PBGF shown in FIG. 3 is obtained. The PBGF may be coated with a resin layer as appropriate.

Next, the obtained PBGF is cut into a predetermined length. In this manner, the first optical filter 20 is produced.

Since the second optical filter 40 is constituted by a PBGF that has a cross sectional shape homologous to that of the first optical filter 20 and an outer diameter slightly different from that of the first optical fiber 20, the second optical filter 40 can be produced by a similar producing method. However, in producing the PBGF constituting the second optical filter 40, the drawing speed is equal but the feed speed of the optical fiber preform is changed as compared to the process of drawing the PBGF constituting the first optical filter 20. In this manner, the PBGF having a cross sectional shape homologous to that of the first optical filter 20 can be obtained. Alternatively, the feed speed of the optical fiber preform may be equal but the drawing speed may be changed as compared to the process of drawing the PBGF constituting the first optical filter 20.

Next, a method for producing the PBGF constituting the wavelength converter 30 will be described.

First, a glass rod doped with a dopant such as germanium and having a higher refractive index than silica glass, which will be the core 31; a silica tube without any dopant, which will be the core region 32; two-layer silica glass rods each having a center portion made of silica glass doped with a dopant such as germanium and having a higher refractive index than silica glass and an outer layer portion made of silica glass provided around the center portion, which will be the high refractive index portions 36; and a silica tube made of silica glass in which a through-hole having a circular cross section is formed, which will be the clad region 37, are prepared. The number of the two-layer silica glass rods to be prepared is the same as that of the high refractive index portions 36.

Next, the silica glass rod to be the core 31 is inserted into the silica tube to be the core region 32. Then, the silica tube to be the core region 32 in which the silica glass rod to be the core 31 is inserted is positioned at the center of the through-hole formed in the silica tube to be the clad region 37. Then, the two-layer silica glass rods are positioned around the silica tube to be the core region 32 in a closely packed manner. In this case, the size of the through-hole is adjusted in advance so that all the two-layer silica glass rods fit into the through-hole of the silica tube.

Next, a lower end of the silica tube in which the silica glass rod to be the core 31, the silica tube to be the core region 32 and the two-layer silica glass rods are arranged is sealed, and a cap is attached to an upper end thereof so that the silica tube is hermetically closed. In this manner, an optical fiber preform is obtained. Then, the optical fiber preform is heated in a heating furnace of a drawing apparatus to draw a fiber while evacuating the silica tube through the cap. Then, the drawn glass is cooled and solidified. In this manner, the PBGF shown in FIG. 5 is obtained. The PBGF may be coated with a resin layer as appropriate.

Next, the obtained PBGF is cut into a predetermined length. In this manner, the wavelength converter 30 is produced.

Although the invention has been described above by reference to a certain embodiment as an example, the invention is not limited thereto.

For example, the PBGFs constituting the first optical filter 20 and the second optical filter 40 are described to have homologous cross sectional structures. However, the cross sectional structures do not necessarily need to be homologous, and the PBGFs constituting the first optical filter 20 and the second optical filter 40 may have different numbers of high refractive index portions 26 from each other, for example.

Figure 10:
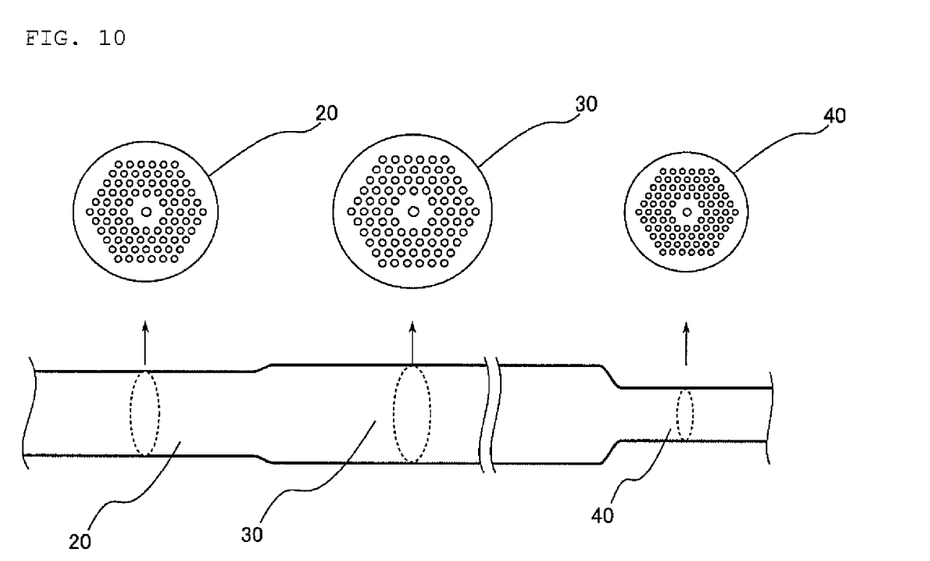
FIG. 10 is a diagram showing a PBGF constituted by the first optical filter, the wavelength converter and the second optical filter that are continuously formed.

In producing the first optical filter 20 and the second optical filter 40, the first optical filter 20 and the second optical filter 40 may be produced from one optical fiber preform. Alternatively, the first optical filter 20, the wavelength converter 30 and the second optical filter 40 may have homologous cross sectional shapes. In this case, the first optical filter 20, the wavelength converter 30 and the second optical filter 40 may be produced continuously from one optical fiber preform. This allows the first optical filter 20, the wavelength converter 30 and the second optical filter 40 to be formed of one PBGF without any fused portions between the first optical filter 20, the wavelength converter 30 and the second optical filter 40 as shown in FIG. 10.

Specifically, the first optical filter 20, the wavelength converter 30 and the second optical filter 40 can be formed of a PBGF whose cross sectional shape is homologous to that of the PBGF shown in FIG. 5. In this case, a specific configuration of the first optical filter 20 is as follows, for example: the PBGF has a diameter of 130 μm, the core has a diameter of 4.2 μm, the relative refractive index difference of the core with respect to silica is 0.7%, the center to center distance of the high refractive index portions is 5.6 μm, the relative refractive index difference of the high refractive index portions with respect to silica is 2.7%, and the high refractive index portions have a diameter of 3.5 μm. In this case, the first optical filter 20 transmits light having a wavelength $\lambda 1$ of 1040 nm, prevents transmission of light having a wavelength $\lambda 2$ of 1090 nm, and prevents transmission of light having a wavelength $\lambda 3$ of 1140 nm.

A specific configuration of the wavelength converter 30 is as follows, for example: the PBGF has a diameter of 136 μm, the core has a diameter of 4.4 μm, the relative refractive index difference of the core with respect to silica is 0.7%, the center to center distance of the high refractive index portions is 5.9 μm, the relative refractive index difference of the high refractive index portions with respect to silica is 2.7%, and the high refractive index portions have a diameter of 3.7 μm. In this case, the wavelength converter 30 transmits light having the wavelength $\lambda 1$ of 1040 nm, transmits light having the wavelength $\lambda 2$ of 1090 nm, and prevents transmission of light having the wavelength $\lambda 3$ of 1140 nm.

A specific configuration of the second optical filter 40 is as follows, for example: the PBGF has a diameter of 105 μm, the core has a diameter of 3.4 μm, the relative refractive index difference of the core with respect to silica is 0.7%, the center to center distance of the high refractive index portions is 4.5 μm, the relative refractive index difference of the high refractive index portions with respect to silica is 2.7%, and the high refractive index portions have a diameter of 2.8 μm. In this case, the second optical filter 40 prevents transmission of light having the wavelength $\lambda 1$ of 1040 nm and transmits light having the wavelength $\lambda 2$ of 1090 nm.

With this configuration, the fiber laser device 100 can have a simple configuration and the production cost thereof can be kept low. Moreover, losses of laser light at boundaries between the first optical filter 20, the wavelength converter 30 and the second optical filter 40 can be reduced and the fiber laser device 100 can output laser light with higher intensity.

In order that the first optical filter 20, the wavelength converter 30 and the second optical filter 40 have homologous cross sectional shapes, the feed speed of the optical fiber preform may be kept constant, and a PBGF may be drawn at a drawing speed adjusted to obtain the first optical filter 20, subsequently, a PBGF may be drawn at a drawing speed adjusted to obtain the wavelength converter 30, and further subsequently, a PBGF may be drawn at a drawing speed adjusted to obtain the second optical filter 40 in drawing the first optical filter 20, the wavelength converter 30 and the second optical filter 40. Alternatively, the drawing speed may be kept constant, and a PBGF may be drawn while the feed speed of the optical fiber preform is adjusted to obtain the first optical filter 20, subsequently, a PBGF may be drawn while the feed speed of the optical fiber preform is adjusted to obtain the wavelength converter 30, and further subsequently, a PBGF may be drawn while the feed speed of the optical fiber preform is adjusted to obtain the second optical filter 40 in drawing the first optical filter 20, the wavelength converter 30 and the second optical filter 40.

In the embodiment described above, a laser oscillator that outputs pulsed laser light is employed as the laser oscillator 10 to obtain a fiber laser device from which pulsed laser light is output. However, pulsed laser light need not necessarily be output, and a laser oscillator that outputs continuous laser light may be employed.

Although the laser oscillator 10 is constituted by a fiber ring laser in the embodiment described above, a fiber ring laser need not necessarily be used. For example, a combination of a fabry-perot type fiber laser in which resonator mirrors are arranged at both ends of a rare earth-doped optical fiber or a semiconductor laser that outputs continuous light and an external modulator may be employed.

In addition, a plurality of pumping light sources 53 may be used in the optical fiber amplifier 50.

INDUSTRIAL APPLICABILITY

According to the invention, a fiber laser device capable of preventing laser light from damaging a laser oscillator even if the laser light is reflected by an object to be irradiated or at an output end.

DESCRIPTION OF REFERENCE NUMERALS

10 . . . laser oscillator
11 . . . pumping light source
12 . . . WDM coupler
13 . . . rare earth-doped fiber
14 . . . optical isolator
15 . . . output coupler
17 . . . band-pass filter
18 . . . optical switch
20 . . . first optical filter
21 . . . first core
22 . . . second core 25 ... periodic structure region
26 ... high refractive index portion
27 ... clad region
30 ... wavelength converter
31 ... core
32 ... core region
35 ... periodic structure region
36 ... high refractive index portion
37 ... clad region
40 ... second optical filter
50 ... optical fiber amplifier
51 ... optical coupler
53 ... pumping light source
55 ... amplification optical fiber
60 ... output end
100 ... fiber laser device

The invention claimed is:

1. A fiber laser device comprising:
a laser oscillator configured to emit laser light having a first wavelength;
a first optical filter to which the laser light having the first wavelength output from the laser oscillator is input and which is configured to transmit the laser light having the first wavelength;
a wavelength converter to which the laser light having the first wavelength that has passed through the first optical filter is input and which is configured to generate laser light having a second wavelength that is longer than the first wavelength using stimulated Raman scattering caused by the laser light having the first wavelength and transmit the laser light having the first wavelength and the laser light having the second wavelength;
a second optical filter to which the laser light having the second wavelength output from the wavelength converter is input and which is configured to transmit the laser light having the second wavelength and prevent transmission of the laser light having the first wavelength;
an optical fiber amplifier to which the laser light having the second wavelength that has passed through the second optical filter is input and which is configured to amplify the laser light having the second wavelength; and
an output end through which the laser light having the second wavelength amplified by the optical amplifier is output, wherein
the first optical filter prevents transmission of the laser light having the second wavelength, and
the first optical filter, the wavelength converter and the second optical filter each include a photonic band gap fiber.

2. The fiber laser device according to claim 1, wherein the wavelength converter is configured to prevent transmission of laser light having a third wavelength longer than the second wavelength generated by stimulated Raman scattering caused by the laser light having the second wavelength.

3. The fiber laser device according to claim 2, wherein the first optical filter is configured to prevent transmission of the laser light having the third wavelength.

4. The fiber laser device according to any one of claims 1 to 3, wherein the first optical filter has a cross sectional shape homologous to that of the second optical filter.

5. The fiber laser device according to any one of claims 1 to 3, wherein the first optical filter, the wavelength converter and the second optical filter are continuously produced from one optical fiber preform.

* * * * *